(12) United States Patent
Inoue

(10) Patent No.: US 9,974,621 B2
(45) Date of Patent: May 22, 2018

(54) MEDICAL SYSTEM AND METHOD OF CONTROLLING MEDICAL TREATMENT TOOLS

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 183 days.

(21) Appl. No.: 15/006,442

(22) Filed: Jan. 26, 2016

(65) Prior Publication Data

US 2016/0213436 A1 Jul. 28, 2016

Related U.S. Application Data

(63) Continuation of application No. PCT/JP2014/068688, filed on Jul. 14, 2014.

(30) Foreign Application Priority Data

Jul. 26, 2013 (JP) .................................. 2013-155771

(51) Int. Cl.
*G06F 19/00* (2018.01)
*A61B 34/37* (2016.01)
(Continued)

(52) U.S. Cl.
CPC ........ *A61B 34/37* (2016.02); *A61B 17/00234* (2013.01); *A61B 17/3421* (2013.01);
(Continued)

(58) Field of Classification Search
CPC . A61B 17/00234; A61B 34/70; A61B 1/0052; A61B 1/008; A61B 17/29;
(Continued)

(56) References Cited

U.S. PATENT DOCUMENTS

2002/0049367 A1 4/2002 Irion et al.
2007/0265502 A1 11/2007 Minosawa et al.
(Continued)

FOREIGN PATENT DOCUMENTS

JP 2002-017752 A 1/2002
JP 2002-360594 A 12/2002
(Continued)

OTHER PUBLICATIONS

International Search Report dated Oct. 7, 2014 issued in PCT/JP2014/068688.
(Continued)

*Primary Examiner* — Ronnie Mancho
(74) *Attorney, Agent, or Firm* — Scully, Scott, Murphy & Presser, P.C.

(57) ABSTRACT

The object of the invention is to automatically adjust the angle of an end effector to improve on the operability of medical treatment tools.

The medical system of the invention comprises a slave medical treatment tool to be controlled and including a moving joint for adjusting the angle of a first end effector relative to a first shaft; a master medical instrument serving as a master control instrument and including a second end effector located at a distal end of a second shaft; a sensor that produces a sensor signal including at least an angle of the second end effector; and a controller that enables follow-up processing for driving a driver such that the angle of the first end effector follows a follow-up criterion set on the basis of a sensor signal produced out of the sensor.

10 Claims, 16 Drawing Sheets

(51) Int. Cl.
  *A61B 17/34*    (2006.01)
  *A61B 34/30*    (2016.01)
  *A61B 17/00*    (2006.01)
  *A61B 17/29*    (2006.01)
  *A61B 34/20*    (2016.01)
  *A61B 90/00*    (2016.01)

(52) U.S. Cl.
  CPC ......... *A61B 17/3462* (2013.01); *A61B 34/20* (2016.02); *A61B 34/30* (2016.02); *A61B 2017/00398* (2013.01); *A61B 2017/2908* (2013.01); *A61B 2017/2927* (2013.01); *A61B 2017/3447* (2013.01); *A61B 2034/2048* (2016.02); *A61B 2034/305* (2016.02); *A61B 2090/067* (2016.02); *A61B 2090/0811* (2016.02)

(58) Field of Classification Search
  CPC ......... A61B 17/3421; A61B 2034/305; A61B 2090/062; A61B 2090/067; A61B 2090/0811; A61B 2017/2927; A61B 2017/2947
  USPC .......................................... 700/258
  See application file for complete search history.

(56) References Cited

U.S. PATENT DOCUMENTS

| | | | |
|---|---|---|---|
| 2007/0276430 A1* | 11/2007 | Lee .................... | A61B 1/00071 606/205 |
| 2012/0004503 A1 | 1/2012 | Kawaura et al. | |
| 2012/0010615 A1* | 1/2012 | Cummings ........ | A61B 18/1445 606/51 |
| 2012/0010616 A1* | 1/2012 | Huang ............... | A61B 18/1445 606/52 |
| 2012/0078248 A1* | 3/2012 | Worrell ............. | A61B 18/1445 606/45 |
| 2013/0110130 A1 | 5/2013 | Manzo et al. | |
| 2013/0131651 A1* | 5/2013 | Strobl ................. | A61B 17/00 606/1 |
| 2014/0239038 A1* | 8/2014 | Leimbach ........ | A61B 17/07207 227/175.1 |
| 2014/0246471 A1* | 9/2014 | Jaworek ........... | A61B 17/07207 227/175.1 |
| 2014/0246473 A1* | 9/2014 | Auld .................... | A61B 17/068 227/175.1 |
| 2014/0246474 A1* | 9/2014 | Hall ................. | A61B 17/07207 227/175.1 |
| 2014/0246475 A1* | 9/2014 | Hall .................... | A61B 17/068 227/175.1 |
| 2014/0246476 A1* | 9/2014 | Hall .................... | A61B 17/068 227/175.1 |
| 2014/0246477 A1* | 9/2014 | Koch, Jr. ............. | A61B 17/068 227/180.1 |
| 2014/0246478 A1* | 9/2014 | Baber ................. | A61B 17/068 227/180.1 |
| 2014/0246479 A1* | 9/2014 | Baber ................. | A61B 17/068 227/180.1 |
| 2014/0249557 A1* | 9/2014 | Koch, Jr. ............. | A61B 17/072 606/170 |
| 2014/0263537 A1* | 9/2014 | Leimbach ........ | A61B 17/07207 227/175.1 |
| 2014/0263538 A1* | 9/2014 | Leimbach ........ | A61B 17/07207 227/175.1 |
| 2014/0263542 A1* | 9/2014 | Leimbach ............ | A61B 17/064 227/175.2 |
| 2014/0263543 A1* | 9/2014 | Leimbach ............ | A61B 17/068 227/175.2 |
| 2014/0263553 A1* | 9/2014 | Leimbach ............ | A61B 17/068 227/176.1 |
| 2014/0263554 A1* | 9/2014 | Leimbach ............ | A61B 17/068 227/176.1 |
| 2014/0263564 A1* | 9/2014 | Leimbach ............. | A61B 34/30 227/180.1 |
| 2014/0263565 A1* | 9/2014 | Lytle, IV ............. | A61B 17/068 227/180.1 |
| 2014/0277017 A1* | 9/2014 | Leimbach ........ | A61B 17/07207 606/167 |
| 2016/0213436 A1* | 7/2016 | Inoue ................. | A61B 17/3421 |
| 2016/0270780 A1* | 9/2016 | Hall .................... | A61B 17/072 |
| 2017/0007255 A1* | 1/2017 | Jaworek ........... | A61B 17/07207 |

FOREIGN PATENT DOCUMENTS

| | | |
|---|---|---|
| JP | 2003-079638 A | 3/2003 |
| JP | 3683554 B2 | 8/2005 |
| JP | 2007-301378 A | 11/2007 |
| JP | 4014792 B2 | 11/2007 |
| JP | 2010-220665 A | 10/2010 |
| JP | 4656700 B2 | 1/2011 |
| WO | 2010/134913 A1 | 11/2010 |

OTHER PUBLICATIONS

Extended Supplementary European Search Report dated Nov. 29, 2016 in related European Patent Application No. 14 82 9992.8.

* cited by examiner

MEDICAL SYSTEM AND METHOD OF CONTROLLING MEDICAL TREATMENT TOOLS

CROSS-REFERENCE TO RELATED APPLICATIONS

This application is a continuation claiming priority on the basis of Japan Patent Application No. 2013-155771 applied in Japan on Jul. 26, 2013 and based on PCT/JP2014/068688 filed on Jul. 14, 2014. The contents of both the PCT application and the Japan Application are incorporated herein by reference.

BACKGROUND OF THE INVENTION AND RELATED ART STATEMENT

The present invention relates to a medical system making use of a medical treatment tool(s) that is inserted through the body of a patient during surgical operation for in vivo treatments, and a method of controlling a medical treatment tool(s).

There is laparoscopic surgery now available wherein various medical instruments inserted through a trocar passed from the body surface of a patient through the body cavity apply various surgical treatments and medical examinations in the body of the patient. Although this laparoscopic surgery is less invasive of patients due to the fact that the size of the body surface site to be cut open may be small, much is left to be desired in the visibility of an endoscope and the operability of medical instruments because there is the need of applying treatments while performing in vivo viewing using the endoscope.

Japanese Patent No. 4014792 discloses that the driver of a treatment portion is driven such that the degree-of-freedom configurations of the treatment portion and an operating portion are aligned in such a way as to make a posture of a medical instrument in the treatment portion identical with a posture of the medical instrument in the operating portion, thereby improving on the operability of the medical instrument.

JP(A) 2007-301378 discloses a therapeutic system designed to detect the tilt angle of a trocar thereby implementing a changeover between the viewing ranges of a viewing device (endoscope) by the distal end of a medical treatment tool.

SUMMARY OF THE INVENTION

A medical system, comprising:
a slave medical treatment tool to be controlled and including a first shaft coupled to a first grip grasped by a user, a first end effector located at a distal end of the first shaft, a moving joint for adjusting an angle of the first end effector relative to the first shaft, and a driver for driving the moving joint;
a master medical instrument serving as a master control instrument and including a second shaft coupled to a second grip grasped by the user and a second end effector located at a distal end of the second shaft;
a first trocar having an insertion opening through which the slave medical treatment tool is inserted;
a second trocar having an insertion opening through which the master medical instrument is inserted;
a sensor for producing out a sensor signal including at least an angle of the second effector; and
a controller that sets a follow-up criterion based on a sensor signal produced out of the sensor and enables follow-up processing for driving the driver such that an angle of the first end effector follows the follow-up criterion.

The invention also provides a method of controlling a medical treatment tool, wherein when a slave medical instrument to be controlled and including a first shaft coupled to a first grip grasped by a user, a first end effector located at a distal end of the first shaft, a moving joint for adjusting an angle of the first end effector relative to the first shaft and a driver for driving the moving joint is inserted through an insertion opening in a first trocar for operation, and a master medical instrument serving as a master control instrument and including a second shaft coupled to a second grip grasped by the user and a second end effector located at a distal end of the second shaft is inserted through an insertion opening in a second trocar for operation, the driver is driven such that an angle of the first end effector follows a follow-up criterion set on the basis of on a sensor that produces a sensor signal including at least an angle of the second end effector.

DETAILED DESCRIPTION OF EMBODIMENTS

Figure 1:
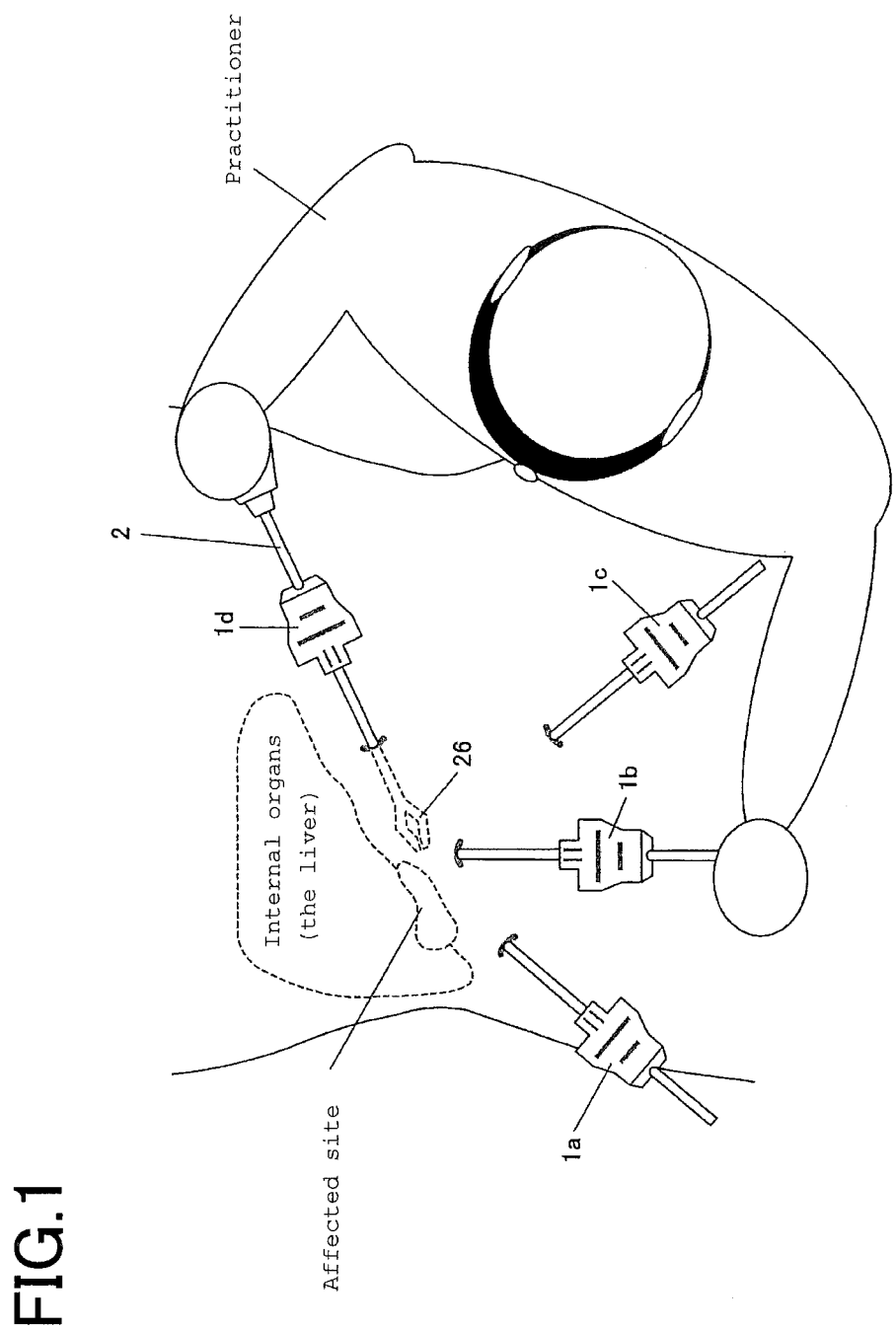
FIG. 1 is illustrative of how laparoscopic surgery is performed using a medical instrument (a pair of forceps).

FIG. 1 is illustrative of how laparoscopic surgery is performed using the forceps 2. In typical laparoscopic surgery, there are multiple openings cut open in the abdomen, etc. of a patient, through which various medical instruments such as an imager (imaging device), forceps and a (electric) knife are inserted to check on images taken by the imager for viewing and surgically treating an affected site or lesion. This laparoscopic surgery can be less invasive of patients because the area to be cut open is small.

In laparoscopic surgery, tubes called the trocars (channels) 1a to 1d are put in openings provided in the body wall of a patient, and various medical instruments are inserted through the patient's body via the trocars 1a to 1d. The forceps 2 (medical treatment tool) are shown to be inserted into the trocar 1d. The forceps 2 placed in the patient's body via the trocar 1d is provided at a distal end with a distal-end grip 26 acting as an end effector so that a practitioner (user) can operate the forceps 2 to open or close the distal-end grip 26 for applying surgical treatments to the affected site.

In conventional medical instruments, the end effector such as the distal-end grip 26 is capable of angular adjustment in the patient's body so as to improve on the operability of the practitioner. The practitioner may operate the end effector to adjust its angle. For laparoscopic surgery performed in the patient's body, it is required for the practitioner to operate the medical instrument while checking on the in vivo states of the patient through an endoscope or the like. However, the angular adjustment of the end effector in the medical instrument including an endoscope is difficult and requires some considerable skill. An object of the invention is to make improvements in the operability of medical instruments in general, and some medical treatment tools in particular that apply treatments to an affected site or the like in the patient's body. As the medical treatment tools, use may be made of not only the forceps 2 shown in FIG. 1 (with a distal-end grip 26 as the end effector) but also an electric knife (with a laser head as the end effector), a water feeder, an aspirator, all used for performing treatments in the patient's body.

Figure 2:
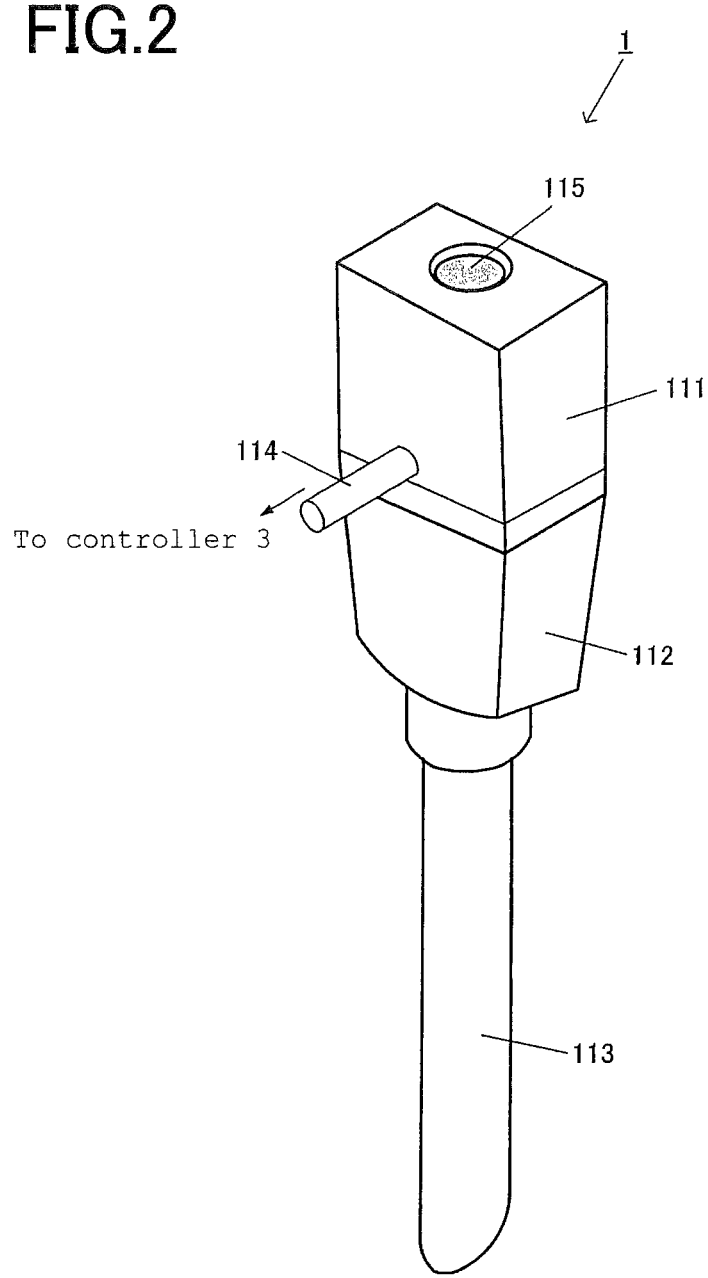
FIG. 2 is illustrative of the outside appearance of the trocar according to one embodiment of the invention.

FIG. 2 is illustrative of the outside appearance of the trocar 1 used with the medical system according to the embodiment described here. This trocar 1 includes or comprises an upper housing 111, a lower housing 112 and a tubular member 113. The upper housing 111 is provided with an opening 115 for insertion of various medical instruments. The tubular member 113 will be inserted in the patient's body. A medical instrument inserted from the opening 115 (hereinafter called the insertion opening 115) passes through the lower housing 112 and tubular member 113, and is inserted from the lower end of the tubular member 113 into the patient's body for in vivo viewing or in vivo treatments.

Within the upper housing 111 there are various sensors disposed for detection of a state of the trocar 1 and a state of a medical instrument inserted from the insertion opening 115. Output signals from various sensors are sent out to a controller 3 by way of a cable 114. Note here that the cable 114 also serves as a power supply to various sensors. Communications between various sensors and the controller 3 may be made by way of such a wire; however, they may be wireless or, alternatively, they may be driven by a battery for removal of the cable 114 from the trocar 1.

Figure 3A:
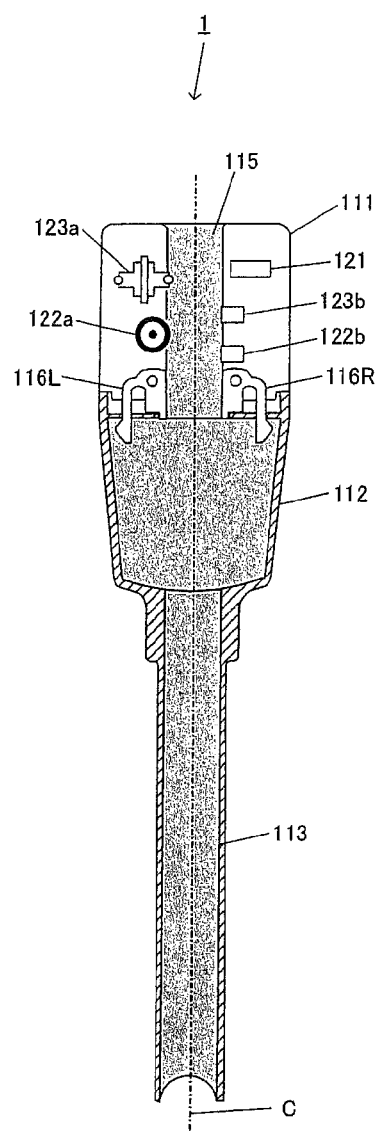
FIGS. 3A and 3B are illustrative of the internal construction of the trocar according to one embodiment of the invention.
Figure 3B:
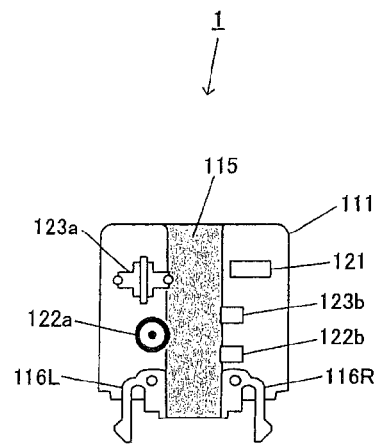

FIGS. 3A-3B are sectional views of the internal construction of the trocar 1 according to the embodiment described here. Referring to FIG. 2, the upper housing 111 is described as being provided with the insertion opening 115. A portion colored in gray in FIG. 2, i.e., a portion from the insertion opening 115 to the lower end of the tubular member 113 is a hollow portion to receive various medical instruments. The upper housing 111 may be coupled to or decoupled from the lower housing 112 by means of couplers 116R and 116L each in a clip form. Note here that the trocar 1 may be formed of a single housing where the upper housing 111 is integral with the lower housing 112. During use of the trocar 1, the upper housing 111 remains coupled to the lower housing 112 by means of the couplers 116R and 116L as shown in FIG. 3A, and for cleaning or other purposes, the upper housing 111 may be decoupled from the lower housing 112, as shown in FIG. 3B. Such coupling/decoupling makes sure easy cleaning, disinfection and replacement of the tubular member 113, and easy maintenance of the upper housing 111 containing various sensors as well.

Referring to the trocar 1 according to the embodiment described here, there are various sensors (a trocar sensor assembly 12) housed within the upper housing 111. The trocar sensor assembly 12 includes a tilt angle detection sensor 121, an amount-of-movement detection sensor 122, and an amount-of-rotation detection sensor 123. The tilt angle detection sensor 121 is provided for detection of a tilt angle indicative of which direction the trocar 1 points in relative to a reference coordinate system. Note here that the reference coordinate system refers to a coordinate system defined for a fixed object such as a patient or a ground plane (see a symbol C in FIG. 9), and various sensors such as an acceleration sensor may be used as the tilt angle detection sensor 121. The acceleration sensor may detect an acceleration applied on it to sense which direction the trocar 1 points in, viz., the angle of tilt relative to the reference coordinate system.

The amount-of-movement detection sensor 122 for detection of the amount of movement is provided to detect the amount of advancement or retraction of the medical instrument through the trocar 1 in the direction of insertion (vertical direction in FIGS. 3A-3B). As described with reference to FIG. 1, a practitioner like a surgeon inserts or extracts the medical instrument through the trocar 1 to move it to a proper site in the patient's body. The amount-of-movement detection sensor 122 may detect the position of the medical instrument inserted through the trocar 1 as an amount of movement. In FIG. 3A, the center axis C of the trocar 1 in the direction of insertion is indicated by an alternate long and short dash line. The amount-of-movement detection sensor 122 detects the amount of movement of the medical instrument in parallel with the center axis C as the amount of movement. In the embodiment described here, the amount-of-movement detection sensor 122 is made up of an amount-of-movement detection roller 122a combined with a photosensor 122b.

The amount-of-rotation detection sensor 123 is provided to detect the amount of rotation of the medical instrument rotating in association with operation by a practitioner or the like. By rotating the medical instrument inserted through the insertion opening 115 about the center axis C, it is possible to change the orientation of the end effector attached to the distal end of the medical instrument in the patient's body. The amount-of-rotation detection sensor 123 may detect this amount of rotation thereby detecting which orientation the end effector of the medical instrument points in. The amount-of-rotation detection sensor 123 may be made up of an amount-of-rotation detection roller 123a combined with a photosensor 123b.

Figure 4:
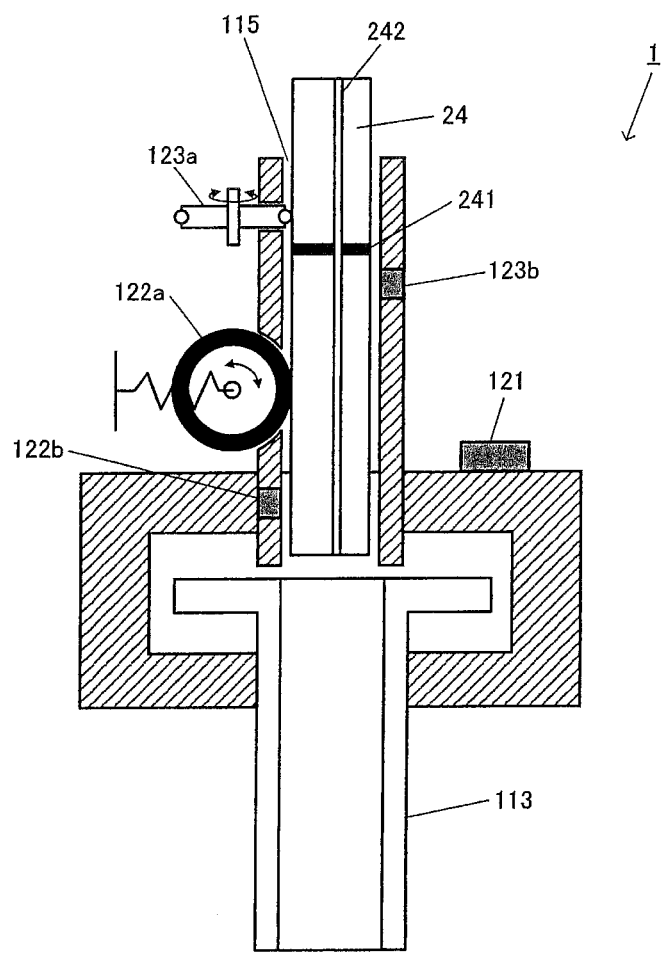
FIG. 4 is illustrative in schematic of the construction of the trocar sensor according to one embodiment of the invention.

Referring to the trocar 1 having the internal construction as described above, the trocar sensor assembly 12 located within the trocar 1 sends a detection signal out to the controller 3 by way of a communication unit 13 not shown in FIGS. 3A-3B. The actuation of the trocar sensor assembly 12 in the embodiment described here is explained with reference to FIG. 4 that is illustrative in schematic of the construction of the trocar sensor assembly 12. FIG. 4 is illustrative in schematic of the construction of the trocar sensor assembly 12 disposed within the trocar 1 shown in FIGS. 3A and 3B, and shows that the first shaft 24 of the medical instrument is inserted through the trocar 1. Note here that the end effector attached to the distal end of the medical instrument or the like is not shown in FIG. 4.

The diameter of the insertion opening 115 in the trocar 1 is somewhat larger than the portion, such as the first shaft 24, of the medical instrument to be inserted in place so that the medical instrument can be inserted through it. Although the trocar 1 will be fixed in the vicinity of the patient's body surface, it is pivotally rotated in association with the operation of the medical instrument with a certain point as a reference. The tilt angle detection sensor 121 fixed on the housing of the trocar 1 may detect pivotal rotation of the trocar 1 thereby detecting the direction of the trocar 1 in the reference coordinate system, viz., the direction of the medical instrument.

As already explained with reference to FIGS. 3A-3B, the amount-of-movement detection sensor 122 is made up of the amount-of-movement detection roller 122a combined with the photosensor 122b. The amount-of-movement detection roller 122a has a direction vertical to the sheet plane of FIG. 4 as a rotating shaft. This amount-of-movement detection roller 122a is biased by a resilient member such as a spring toward the insertion opening 115 so that it comes in contact with the surface of the medical instrument (first shaft 24) inserted through the insertion opening 115 to convert the amount of movement of the medical instrument into the amount of its rotation. The amount-of-movement detection roller 122a is provided at the rotating shaft with an encoder that produces the amount of rotation of the amount-of-movement detection roller 122a in the form of the amount of movement. In the embodiment described here, the photosensor 122b is positioned facing the inside of the insertion opening 115 to calibrate the amount of movement (or set it to the initial value). This photosensor 122b detects a position-of-movement detection mark 241 provided on the medical instrument side (or the first shaft 24 side or the like) so that the amount of movement detected by the amount-of-movement detection roller 122a is calibrated. Accordingly, when the medical instrument advances or retracts through the insertion opening 115, the amount of movement is calibrated (or set to its initial value) each time the position detection mark 241 passes through the photosensor 122b so that the precise amount of movement of the medical instrument relative to the trocar 1 can be detected.

The amount-of-rotation detection sensor 123 in the embodiment described here is made up of the amount-of-rotation detection roller 123a with the photosensor 123b as explained with reference to FIGS. 3A-3B. The amount-of-rotation detection roller 123a has a rotating shaft pointing in the vertical direction of FIG. 4. The amount-of-rotation detection roller 123a is biased by a resilient member such as a spring toward the insertion opening 115 so that it comes into contact with the surface of the medical instrument (first shaft 24) to convert the amount of rotation of the medical instrument into the amount of rotation of the amount-of-rotation detection roller 123a. Note here that the contact surface of the amount-of-rotation detection roller 123a is preferably provided with a member (such as a bearing) that does not disturb the movement of the medical instrument in the insertion direction. The amount-of-rotation detection roller 123a is provided at the rotating shaft with an encoder that produces the amount of rotation of the amount-of-rotation detection roller 123a in the form of the amount of rotation of the medical instrument. In the embodiment described here, the photosensor 123b facing the inside of the insertion opening 115 is provided to calibrate the amount of rotation (or set it to the initial value). This photosensor 123b detects a position-of-rotation detecting mark 242 provided on the medical instrument side (the first shaft 24 or the like) so that the amount of rotation detected by the amount-of-rotation detection roller 123a can be calibrated as is the case with the amount-of-movement detection sensor 122.

While the trocar sensor assembly disposed within the trocar 1 is explained, it is to be understood that the sensor may be configured in various forms. In the embodiment described here, for instance, a mechanical sensor configuration using a roller is adopted to detect the amount of movement and the amount of rotation. It is to be understood, however, that an optical sensor capable of detecting the amount and direction of movement of a surface, for instance, an optical sensor used with a laser mouth may also be used for detection of the amounts of movement and rotation. In that case, just one optical sensor may be used to detect the amount of movement and the amount of rotation. For the medical system according to the embodiment described here, it is necessary to determine the direction or the direction and position of the medical instrument inserted through the patient's body. In the embodiment described here, these are detected by various sensors housed within the trocar 1 in view of ease of handling; however, the direction or the direction and position of the medical instrument may be detected by sensors located outside of the trocar 1. For instance, the tilt angle detection sensor 121 located in the trocar 1 may be located directly on the medical instrument side.

Figure 5A:
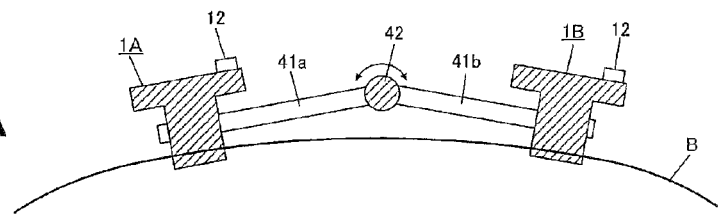
FIGS. 5A, 5B and 5C are illustrative in schematic of various constructions of the relative position sensor according to one embodiment of the invention.
Figure 5B:
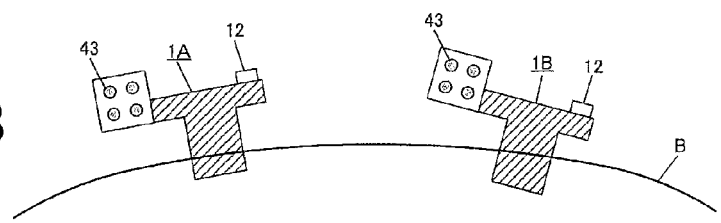
Figure 5C:
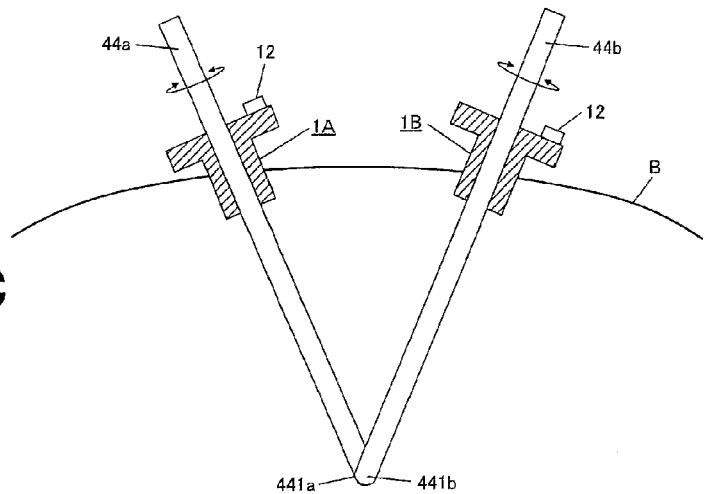

In the medical system according to the embodiment of the invention, there is follow-up processing implemented in which the movement of the master medical instrument (master control instrument) inserted through one trocar 1 is detected to control motion of the slave medical treatment tool (to be controlled) inserted through another trocar 1. Note here that the master medical instrument includes, in addition to a medical treatment tool, a medical instrument such as an endoscope that does not apply any treatment to a patient's affected site. For such follow-up processing, it is required to have a grip of relative positions between the trocars 1 and align coordinates of measurement signals obtained from the trocar sensor assembly 12 in each trocar 1. FIGS. 5A-5C are illustrative in schematic of various configurations of relative position sensors for detecting the relative positions between multiple trocars 1A and 1B attached to the patient's body surface.

FIG. 5A shows a mode of coupling trocars 1A and 1B by rotatable arms 41a and 41b. The arms 41a and 41b are coupled together by a moving joint 42 in such a way as to be movable. An output signal indicative of a joint angle is produced out to a controller (not shown). On the basis of the output signal from the moving joint 42, it is possible to mechanically detect the relative positions between both the trocars 1A and 1B.

FIG. 5B shows a mode of locating a position detecting mark 43 in each trocar 1A, 1B. After the trocars 1A and 1B are attached to the body surface, the position detecting marks 43 are taken by a camera or the like to detect the positions of the position detecting marks 43 so that the relative positions between both the trocars 1A and 1B can be optically detected.

FIG. 5C is illustrative of how to detect the relative positions between both the trocars 1A and 1B by inserting jigs 44a and 44b through both. The jigs 44a and 44b inserted through the trocars 1A and 1B are provided at the distal ends with couplers 441a and 441b capable of coupling both together. After insertion of the jigs 44a and 44b through the trocars 1A and 1B, the couplers 441a and 441b are coupled together in the body. Coupling of the jigs 44a and 44b makes sure coordinated motion of the trocars 1A and 1B. In this state, the jigs 44a and 44b are operated to rotate the trocars 1A and 1B to acquire output signals from the trocar sensor assembly 12 in multiple states. In consideration of conditions in the coupled state, convergent calculation may be performed with respect to the output signals acquired in the multiple states to detect the relative positions between the trocars 1A and 1B. After implementation of such relative position detection processing, the jigs 44a and 44b are dismounted to insert the medical instrument for the start of medical treatment.

In the modes of FIGS. 5A and 5B, the relative positions between the trocars 1A and 1B may be detected even during medical treatment. In the mode of FIG. 5C, the relative position detection processing may be implemented using the jig 44a before the start of medical treatment to detect the relative positions between both the trocars 1A and 1B. Alternatively, the relative positions between both the trocars 1 may simply be aligned without recourse to the relative position sensor or relative position detection processing. Alignment between multiple trocars 1 is explained with reference to FIG. 6. In the medical system of the invention, determination of which direction the trocars point in, i.e., the direction of the medical instrument or treatment tool inserted through the trocars 1 may be all that is needed. In other words, it is possible to align coordinate systems of signals produced by tilt angle detection sensors 121 mounted on the trocars 1 to keep coordinate systems of output signals from multiple trocars 1 in alignment.

Figure 6:
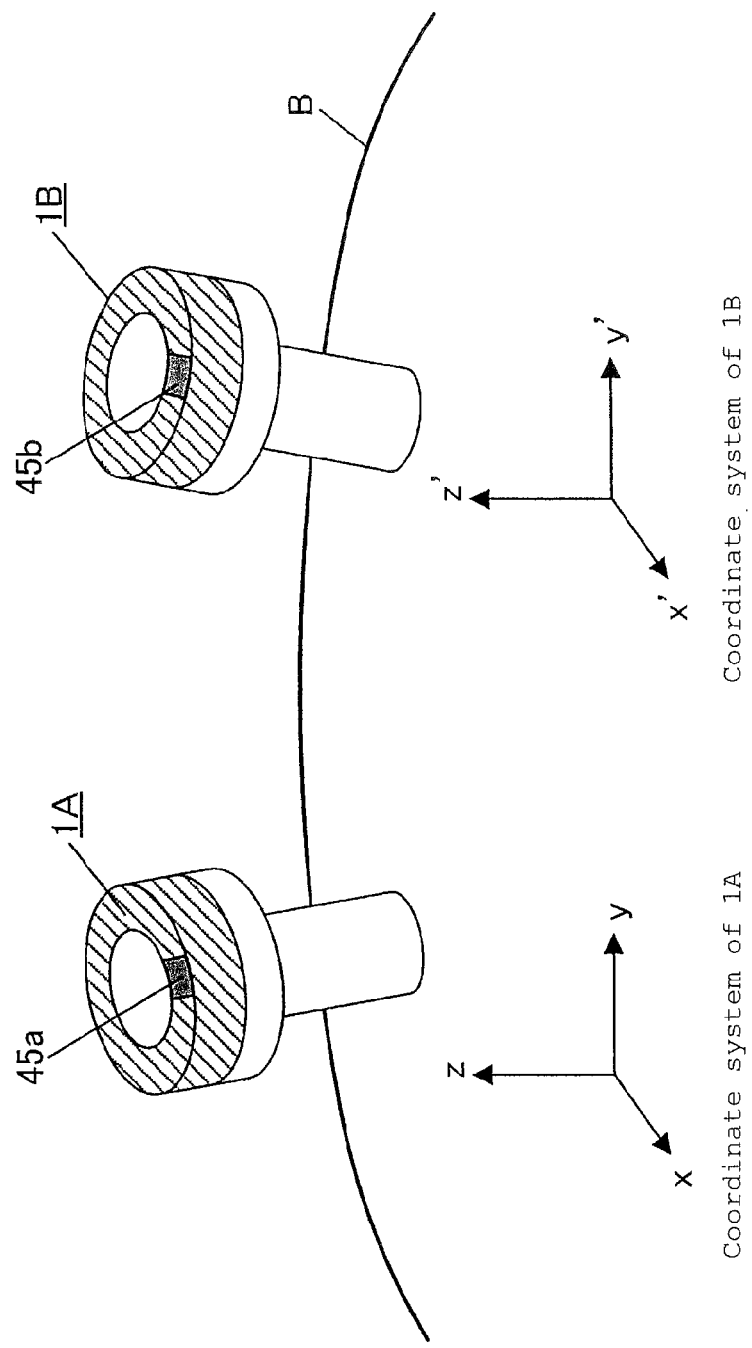
FIG. 6 is illustrative of alignment of the trocars according to one embodiment of the invention.

To align the coordinate systems of signals produced out of the trocars 1 in the embodiment shown in FIG. 6, the trocars 1A and 1B are provided with direction detecting marks 45a and 45b indicative of given directions on the coordinates of signals produced out of an acceleration sensor. While checking on the direction detecting marks 45a and 45b, the practitioner attaches the trocars 1A and 1B on the patient's body surface B in such a way as to be kept in alignment. Attached to the body surface B, the trocars 1A and 1B may possibly tilt, but the directions of the direction detecting marks 45a and 45b may be held in alignment to keep the coordinate systems of output signals from the trocars 1A and 1B in substantial alignment because the output signals of the tilt angle detection sensors 121 located in the trocars 1A and 1B have coordinate systems having the direction of gravity as a reference.

Figure 7A:
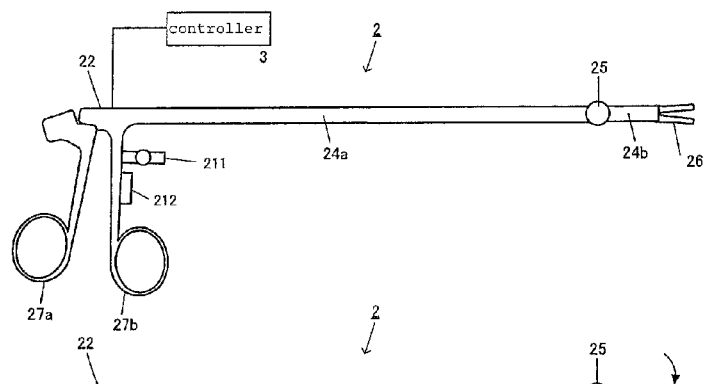
FIGS. 7A, 7B and 7C are illustrative of the construction and control mode of the medical treatment tool (forceps) according to one embodiment of the invention.
Figure 7B:
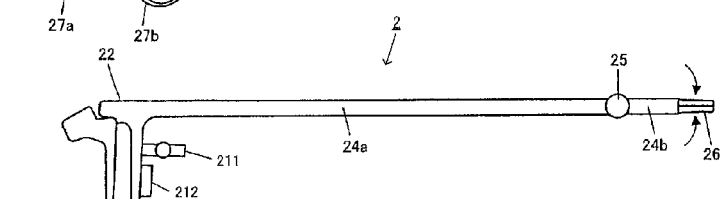
Figure 7C:
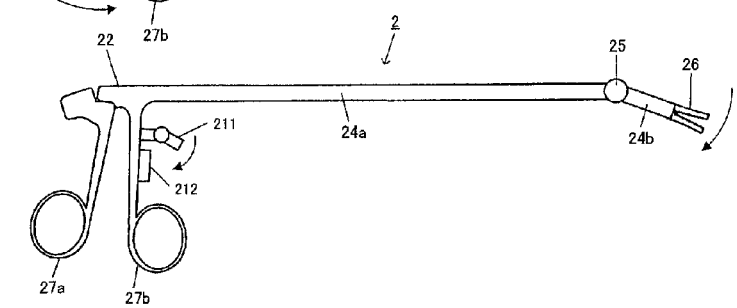

The medical treatment tool(s) used in the medical system according to one embodiment of the invention is now explained. FIGS. 7A-7C are illustrative of the construction and control mode of the medical treatment tool 2 (forceps) according to one embodiment of the invention. In the present disclosure, the medical treatment tool 2 is understood to refer to the one that is inserted through the patient's body via the trocar 1 to perform treatments in the patient's body. The medical treatment tool 2 includes, in addition to a pair of forceps shown in FIGS. 7A-7C, medical knives (inclusive of an electric knife), water supply pipes, aspirators, etc. On the other hand, the medical instrument is not included in the medical treatment tool 2; it is designed to view in-vivo states of the patient and not used at all for treatments such as endoscopes and various sensors for taking in vivo measurements in the patient's body.

The medical treatment tool 2 (a pair of forceps) in the embodiment of the invention shown in FIGS. 7A-7C performs various treatments in the patient's body, and comprises a distal-end grip 26 as an end effector. This distal-end grip 26 comprises a pair of grip members 27a and 27b put by a string (such as a wire, thread or rod) in coordinated operation. As depicted in FIG. 7A, the distal-end grip 26 remains open while the grip members 27a and 27b are spaced away from each other, and as depicted in FIG. 7B, the distal-end grip 26 remains closed while the grip members 27a and 27b get proximate to each other. The practitioner may open or close the grip members 27a and 27b while grasping them to operate the opening and closing of the distal-end grip 26.

In the embodiment described here, the forceps 2 include a first shaft 24a and a second shaft 24b capable of rotation by way of a moving joint 25. As the moving joint 25 is rotated using the driver 22 built in the main body of the medical treatment tool 2, it may cause the second shaft 24b to which the distal-end grip 26 (end effector) is attached to rotate relative to the first shaft 24a. The driver 22 may be a motor or otherwise constructed in various configurations capable of generating driving force in response to a control signal from the controller 3. The driving force generated in the driver 22 is transmitted to the moving joint 25 via a driving force transmission means such as a gear, a wire or a thread to rotate the second shaft 24b to which the distal-end grip 26 is attached. In the embodiment described here, the driver 22 is shown to be built in the main body of the medical tool instrument 2; however, it may be located outside of the main body of the medical treatment tool 2. FIG. 7A shows one exemplary mode of connecting the medical instrument 2 to the controller 3. The connection mode to the controller 3 is the same as in FIGS. 7B and 7C although not shown. In the embodiment described here, a direction input portion 211 is provided on the grip member 27b. As the direction input portion 211 is operated, it causes an operational signal to be sent to the controller 3 that in turn drives the driver 22 for control of rotation of the moving joint 25. In the embodiment described here, the driver 22 may be controlled in a spontaneous way without recourse to the operation of the direction input portion 211. As the direction input portion 211 in a stick form is operated as shown in FIG. 7C, it causes the driver to rotate the moving joint 25 in association with its operating direction, resulting in a change in the orientation of the distal-end grip 26. While the moving joint 25 is shown to be capable of two-dimensional motion on the sheet plane, it is to be noted that it is also capable of three-dimensional motion including a direction diagonal to the sheet plane.

Referring to the medical treatment tool 2 (forceps) according to the embodiment described here, just one moving joint 25 is used for control of the orientation of the distal-end grip 26 (end effector), but it is to be understood that the direction or orientation control of the distal-end grip 26 may be carried out by multiple moving joints.

Figure 8:
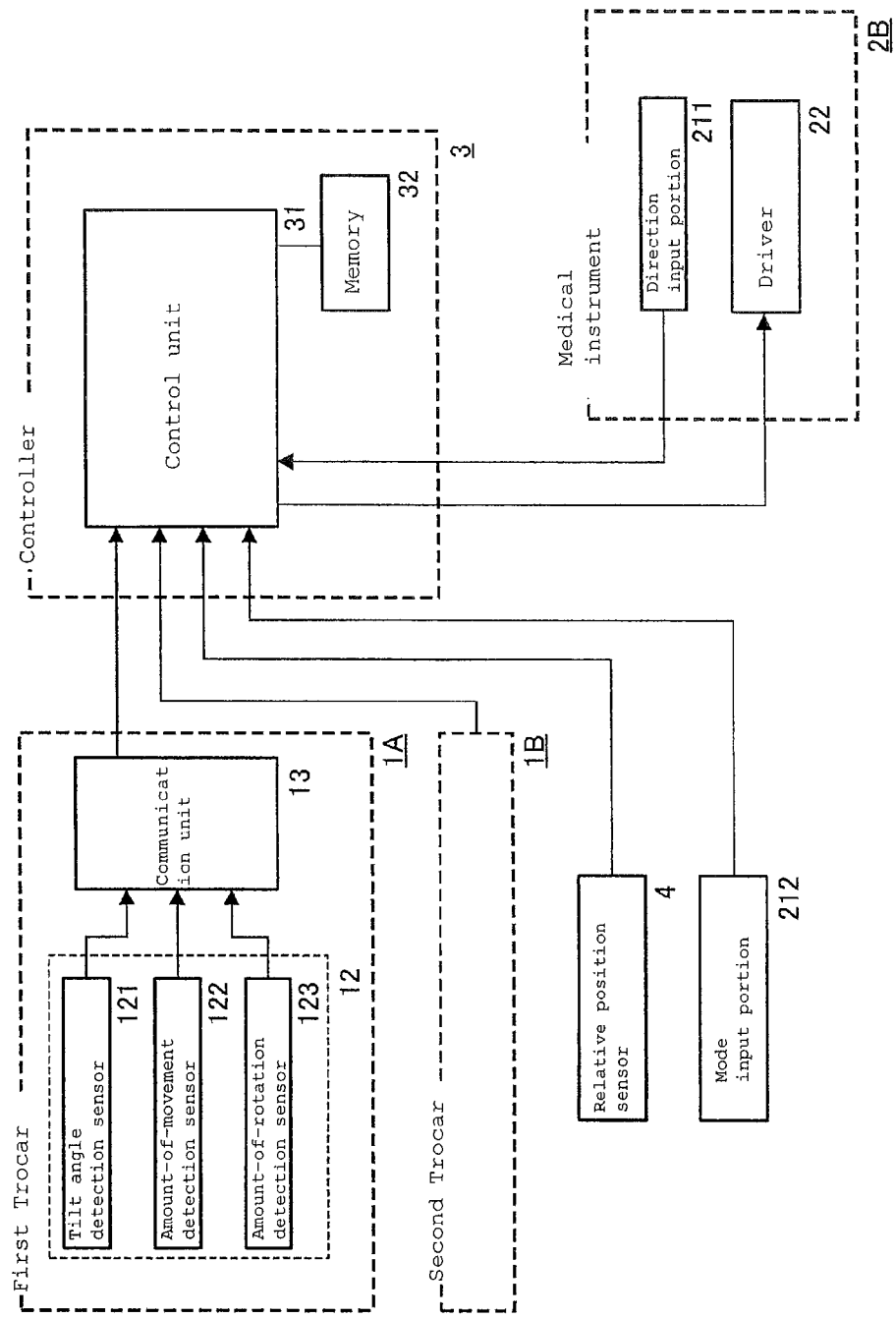
FIG. 8 is a block diagram for the control configuration of the medical system according to one embodiment of the invention.

FIG. 8 is a block diagram for the control configuration of the medical system according to one embodiment of the invention. This medical system includes or comprises the first and second trocars 1A and 1B explained with reference to FIGS. 2, 3A, 3B and 4, the relative position sensor 4 explained with reference to FIGS. 5A-5C, and the medical treatment tool 2 and controller 3 explained with reference FIGS. 7A-7C. Note here that the relative position sensor 4 may be dispensed with when the relative position detection processing using the jigs as shown in FIG. 5C or the alignment of the directions of the coordinate systems of both the trocars 1A and 1B by the direction detecting marks 45a and 45b as shown in FIG. 6 is all that is needed for control.

The first trocar 1A includes or comprises a tilt angle detection sensor 121, an amount-of-movement (advancement and retraction) detection sensor 122, an amount-of-rotation detection sensor 123 forming a part of the trocar sensor assembly 12, and a communication unit 13. While the internal construction of the second trocar 1B is not shown, it is to be understood that it is constructed as is the case with the first trocar 1A. Note here that although depending on the control mode, all of the (three) sensors are not necessarily used for the trocar sensor assembly 12. The control mode will be described later. On the other hand, the medical treatment tool 2 to be controlled includes or comprises a direction input portion 211 as the operation input unit 21, a mode input portion 212, and the driver 22. The driver 22 may be a motor or other like member capable of generating driving force to the moving joint 25 of the medical treatment tool 2. Further, the mode input portion 212 is provided as the operation input. The mode input portion 212 may be provided on the grip member 27b shown in FIGS. 7A-7C or, alternatively, it may be separately provided in the form of a footswitch or the like. This mode input portion 212 is used for a changeover between various modes implemented in the medical system.

The first and second trocars 1A, 1B and medical treatment tool 2B are connected to the controller 3. The controller 3 includes or comprises a control unit 31 constructed of a CPU or the like, and a memory 32 serving as a storage. Various programs running on the medical system may be stored in the memory 32 in which various signals and data necessary for running programs may also be stored.

The controller 3 according to the embodiment described here may run in two modes. In one (operating) mode, the direction input portion 211 of the medical treatment tool 2B to be controlled is operated such that the moving joint 25 is rotated to adjust the angle of the end effector. In this mode, the practitioner may operate the direction input portion 211 such that the moving joint 25 is rotated to adjust the angle of the distal-end grip 26 (end effector) as explained with reference to FIG. 7C. While viewing affected sites or lesions in the body through the endoscope or the like, the practitioner may operate the direction input portion 211 to turn or point the distal-end grip 26 in a proper direction.

In another (follow-up) mode, follow-up processing is implemented such that the angle of the distal-end grip 26 (end effector) of the medical treatment tool 2B to be controlled is adjusted in a proper direction depending on the position of the end effector of the master medical treatment tool. In this mode, the driver 22 is driven such that the angle of the distal-end grip 26 (end effector) of the medical treatment tool 2B to be controlled traces up the follow-up criterion (reference direction or reference point) corresponding to the end effector of the medical instrument detected by the trocar sensor 12 assembly of the first trocar 1A.

Figure 9:
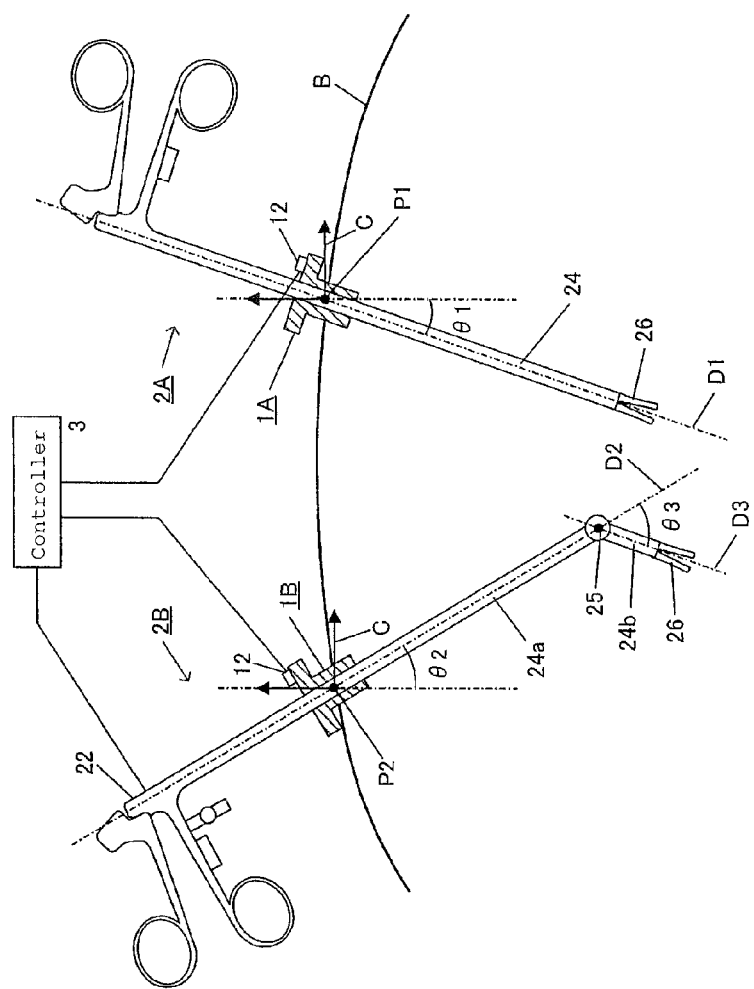
FIG. 9 is illustrative of the control mode (Example 1) of the medical treatment tool according to one embodiment of the invention.

FIG. 9 shows the control configuration of the follow-up mode (Example 1) in which the medical instrument 2 (forceps) explained with reference to FIGS. 7A-7C is to be controlled. In Example 1, the master medical treatment tool 2A (forceps) is inserted through the first trocar 1A, and the trocar sensor assembly 12 of the first trocar 1A is capable of detecting a direction in which the medical treatment tool 2A points relative to a reference coordinate system C. On the other hand, the medical treatment tool 2B to be controlled is inserted through the second trocar 1B. The trocar sensor assembly 12 of the second trocar 1B is capable of detecting a direction in which the medical treatment tool 2B points relative to the reference coordinate C. Note here that the reference coordinate system C of the trocar sensor assembly 12 of the first trocar 1A and the reference coordinate system C of the trocar sensor assembly 12 of the second trocar 1B are held in alignment by means of the relative position sensor between the trocars 1 explained with reference to FIGS. 5A-5C or by aligning them as explained with reference to FIG. 6 (as is the case with other examples). The medical treatment tool 2B and the two trocar sensors assembly 12 are connected to the controller 3, and the controller 3 is capable of detecting various states of the trocars 1A, 1B and medical treatment tools 2A, 2B, and driving and controlling the driver 22 of the medical treatment tool 2B. In the follow-up mode according to the embodiment described here, the orientation of the distal-end grip 26 of the medical treatment tool 2B inserted through the second trocar 1B is controlled in association with fluctuations of the direction of the medical treatment tool 2A inserted through the first trocar 1A. To be specific, the moving joint 25 is controlled by the driver 22 such that a direction D1 (follow-up criterion) in which the distal-end grip 26 of the medical treatment tool 2A points is kept parallel with a direction D3 in which the distal-end grip 26 of the medical treatment tool 2B points.

In the follow-up control mode of keeping D1 and D3 in parallel with each other, a control angle $\theta 3$ of the moving joint 25 in the medical treatment tool 2B (the angle of the second shaft 24b with respect to the first shaft 24a) may be computed out of the sum of an angle $\theta 1$ detected by the trocar sensor 12 assembly of the first trocar 1A and an angle $\theta 2$ detected by the trocar sensor assembly 12 of the second trocar 1B. The controller 3 detects the angles $\theta 1$ and $\theta 2$ produced out of the respective trocar sensor assemblies 12 and drives the driver 22 such that the moving joint 25 forms the control angle $\theta 3$ so that even when the medical treatment tool 2A is operated, both the distal-end grips 26 are kept in parallel with each other. While the moving joint 25 is shown in FIG. 9 to move two-dimensionally on the sheet plane, it is to be noted that the follow-up processing may trace up three-dimensional motion including a direction vertical to the sheet plane, too. In that case, the angle of rotation of the amount-of-rotation detection sensor 123 of the second trocar 1B must be taken into account because the orientation of the distal-end grip 26 changes in association with the rotation of the medical treatment tool 2B about its insertion direction.

With reference to the control configuration of FIG. 8, as the operating mode is designated by the mode input portion 212, it causes the driver 22 of the medical treatment tool 2B to adjust the angle of the moving joint 25 based on an operational signal from its direction input portion 211. As the follow-up mode is designated by the mode input portion 212, on the other hand, it causes the controller 3 to implement follow-up processing of controlling the driver 22 for the medical treatment tool 2B on the basis of a sensor signal produced out of the trocar sensor assembly 12 of the first trocar 1A. In this follow-up processing, the driver 22 is controlled such that the end effector of the medical treatment tool 2B keeps holding a given position relation to the follow-up criterion set on the medical instrument 2A.

In the follow-up mode explained with reference to FIG. 9, control is implemented such that the distal-end grip 26 of the master medical treatment tool 2A and the distal-end grip 26 of the slave medical treatment tool 2B (to be controlled) are parallel with each other in terms of orientation. For instance, such a control mode makes sure smooth medical needle passing between both the medical treatment tools 2A and 2B because a medical needle can be grasped by both the distal-end grips 26 from the same direction. The follow-up control mode is not limited to such a configuration; the follow-up control may be implemented in various configurations. For instance, the angles formed by both the distal-end grips 26 may not be parallel, or they may be adjusted using an input portion such as a dial.

Figure 10:
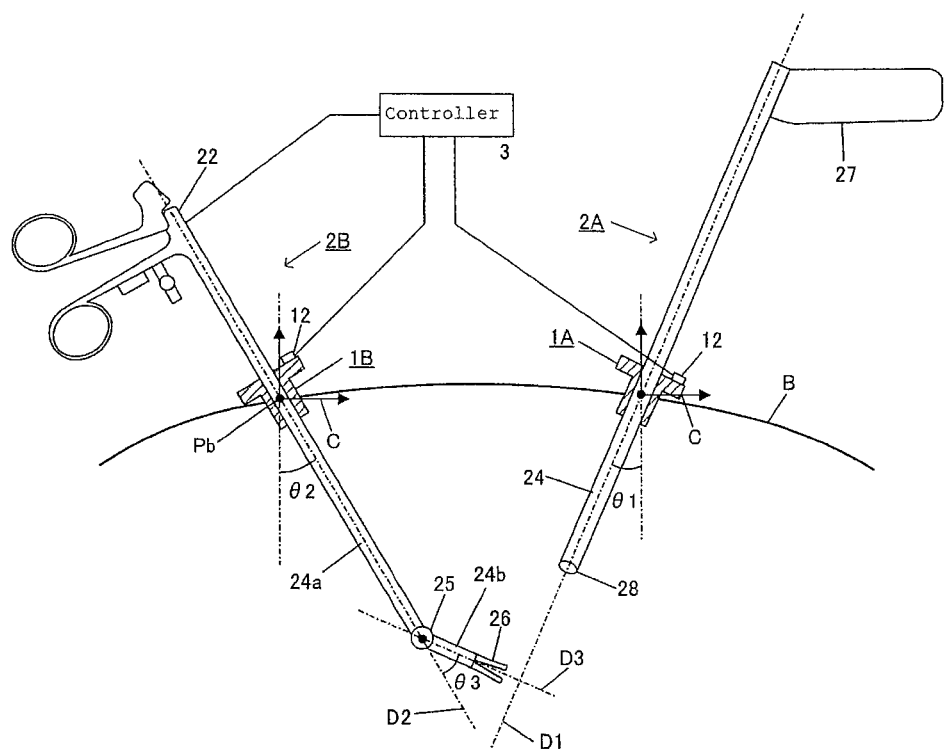
FIG. 10 is illustrative of the control mode (Example 2) of the medical treatment tool according to one embodiment of the invention.

FIG. 10 shows a control mode (Example 2) of controlling medical treatment tools according to another embodiment of the invention. In Example 2, the medical instrument 2A (endoscope) is used as the master, and the medical treatment tool 2B (a pair of forceps 2B) is used as the slave to be controlled. The shaft 24 of the master medical instrument 2A is provided at its distal end with an imager 28 as an end effector. A practitioner performs treatments while viewing an affected site image taken by the imager 28. In follow-up processing, the slave medical treatment tool 2B rotates the moving joint 25 such that a direction D3 in which the distal-end grip 26 points is at a given angle (the right angle here) relative to the imaging axis direction D1 of the imager 28 of this medical instrument 2A. Such a control mode contributes more to the operability of the medical treatment tool 2B because the orientation of the distal-end grip 26 is controlled in alignment with a viewing position of the imager 28.

Figure 11:
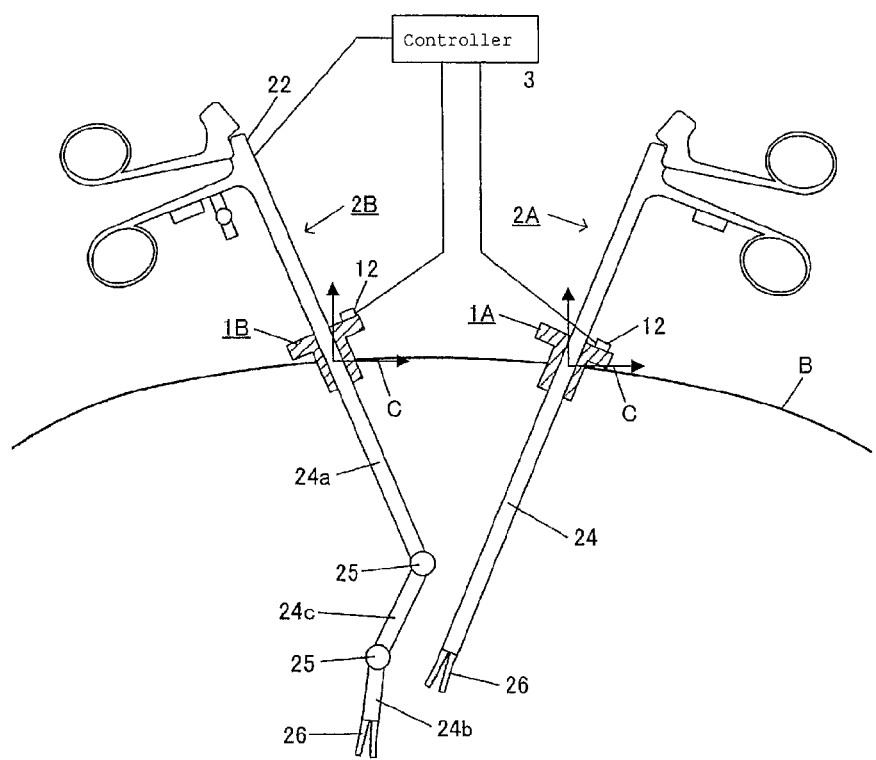
FIG. 11 is illustrative of the control mode (Example 3) of the medical treatment tool according to one embodiment of the invention.

FIG. 11 shows a control mode (Example 3) of control medical treatment tools according to yet another embodiment of the invention. In Example 3, the medical treatment tool 2A (a pair of forceps) is used as the master, and the medical treatment tool 2B (a pair of forceps) is used as the slave (to be controlled) too. The slave medical treatment tool 2B comprises a plurality of moving joints 25. Such a control mode makes sure prevention of the medical treatment tool 2A from coming into contact with the medical treatment tool 2B because the respective moving joints 25 of the slave medical treatment tool 2B are driven depending on the position of the master medical treatment tool 2A. The controller 3 controls the respective moving joints 25 on the medical treatment tool 2B side in such a way as to prevent contact of the medical treatment tools 2A and 2B, depending on the position of the medical treatment tool 2A determined on the basis of a sensor signal from the first trocar 1A and the position of the medical treatment tool 2B determined on the basis of a sensor signal from the second trocar 1B.

Figure 12:
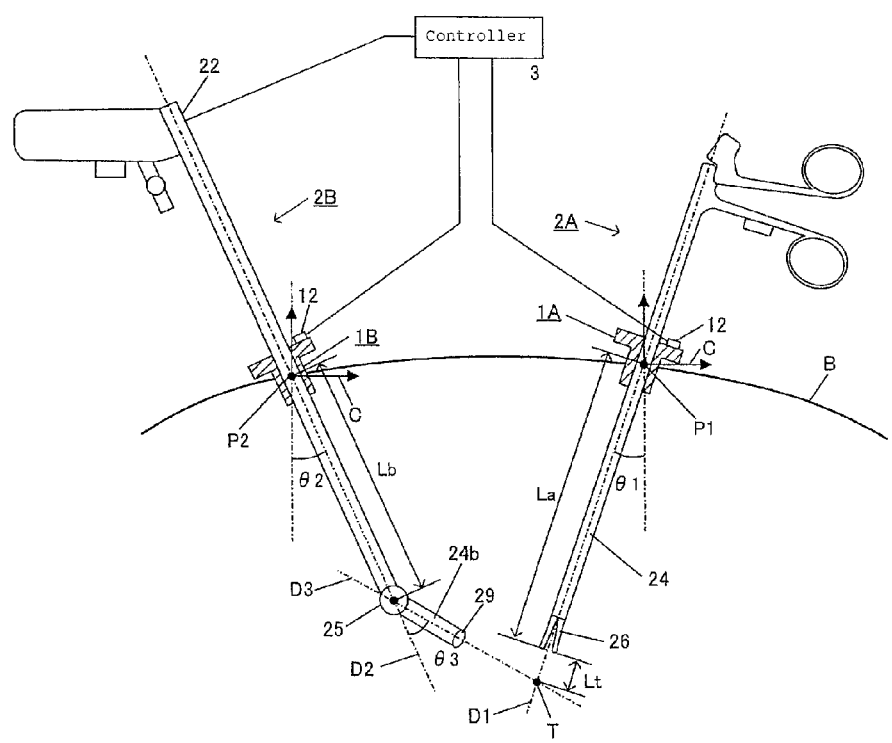
FIG. 12 is illustrative of the control mode (Example 4) of the medical treatment tool according to one embodiment of the invention.

FIG. 12 shows a control mode (Example 4) of controlling medical treatment tools according to a further embodiment of the invention. In Example 4, the medical treatment tool 2A (a pair of forceps) is used as the master, and the medical treatment tool 2B (water feeder) having a water feed portion 29 is used as the slave (to be controlled). The water feeder 2B feeds water, chemicals and so on for washing, staunching and so on of an affected site. The water feed portion 29 (end effector) of the medical treatment tool 2B is controlled in such a way as to point toward a reference point T (follow-up criterion) depending on the direction of the distal-end grip 26 (end effector) of the master medical treatment tool 2A. Such a control mode contributes more to practitioner's operability, because when the practitioner uses the master medical treatment tool 2A to apply treatments to the reference point T such as an affected site, the water feed portion 29 feeds water or the like following the control point T.

In Example 4, it is necessary for the first trocar 1A to detect an amount of movement La of the medical treatment tool 2A because there is the reference point T set relative to the distal-end grip 26 of the master tool. The reference point T is set on the basis of the amount of movement La, an angle $\theta1$ and a distance Lt from the distal-end grip 26 detected by the trocar sensor assembly 12. Note here that the distance Lt may be a fixed value or, alternatively, it may be set by operation of the input unit. Of the slave medical treatment tool 2B, too, the amount of movement Lb, angle $\theta2$ and so on are detected by the trocar sensor assembly 12. On the basis of the results of detection by each trocar sensor 12, the control angle $\theta3$ of the water feeder 29 as the end effector is determined to control the driver 22.

In Examples 1 to 4 as described above, the master medical instrument 2A or medical treatment tool 2A has a structure free from the moving joint 25, but the master instrument or tool may be provided with the moving joint 25 too. In that case, the medical treatment tool 2A may be used as the master tool in such a way as to be optionally changed over to the slave tool to be controlled.

Figure 13:
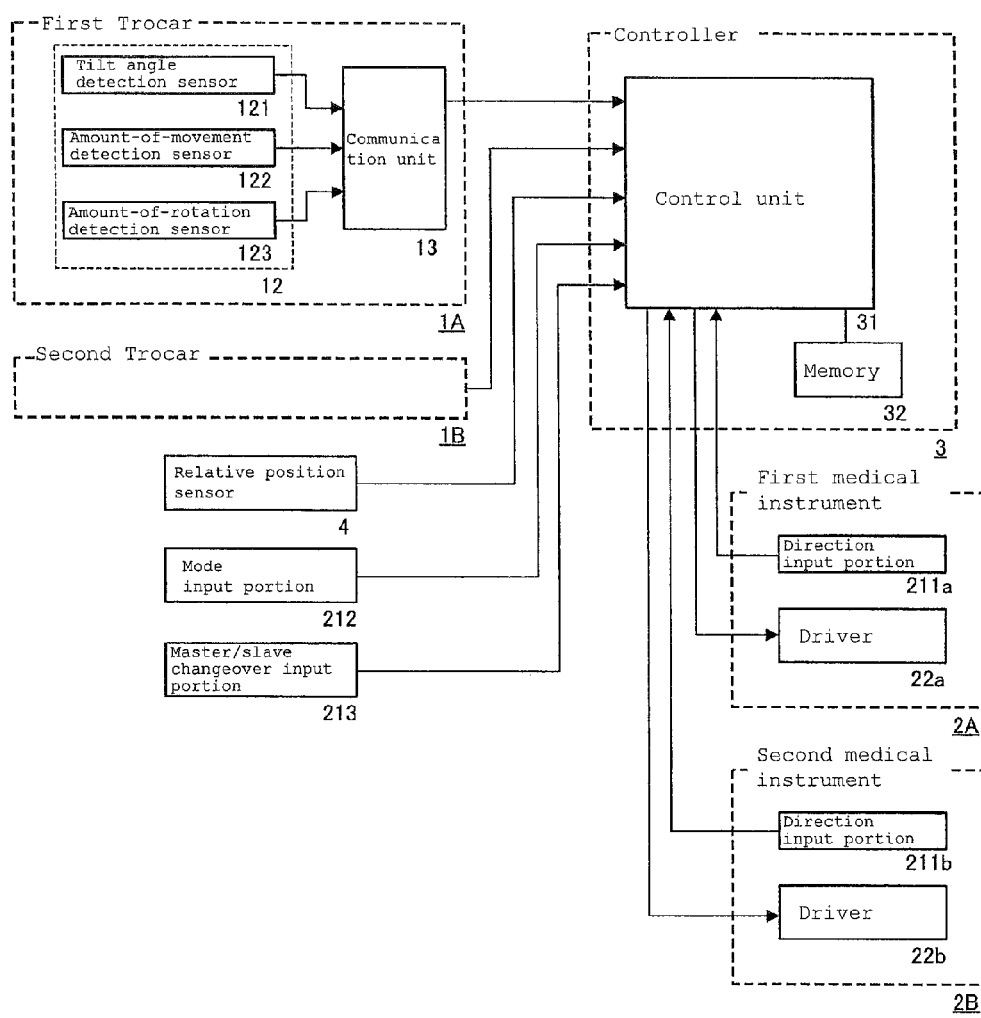
FIG. 13 is a block diagram for the control configuration of the medical system according to one embodiment of the invention.

FIG. 13 is a block diagram for the control configuration of the medical system according to a further embodiment of the invention. This embodiment is different from the mode explained with reference to FIG. 8, etc. in that both 2A and 2B are medical treatment tools and there is a master/slaver changeover input portion 213 provided.

Figure 14:
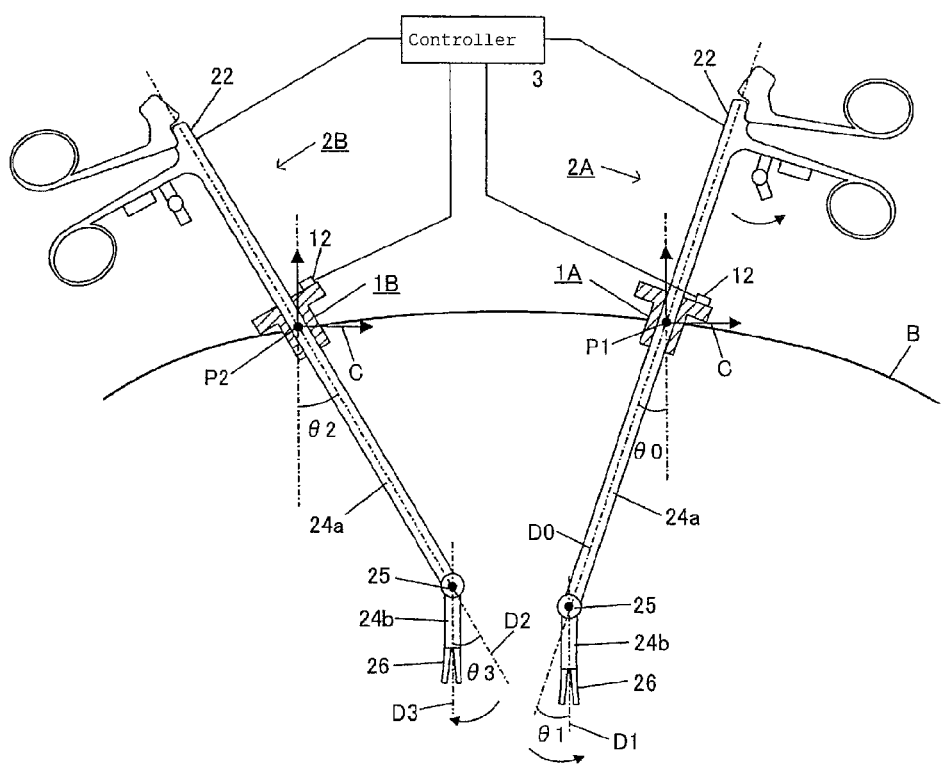
FIG. 14 is illustrative of the control mode (Example 5) of the medical treatment tool according to one embodiment of the invention.

Referring to FIG. 14, both 2A and 2B are indicative of medical treatment tools (forceps). The medical treatment tools 2A, 2B and trocar sensors 12 are connected to the controller 3. The controller 3 is capable of detecting various states of the trocars 1A, 1B and medical treatment tools 2A, 2B, and driving and controlling the drivers 22 of the medical treatment tools 2A and 2B. As in the foregoing examples, the medical treatment tool 2A is set as the master whereas the medical treatment tool 2B is set as the slave to be controlled. In follow-up processing, the medical treatment tool 2A may be operated for movement of the distal-end grip 26. In the embodiment described here, the direction input portion 211a of the medical treatment tool 2A may then be operated to rotate the moving joint 2 for adjustment of the angle of the distal-end grip 26. In the follow-up processing according to the embodiment described herein, the distal-end grip 26 of the medical treatment tool 2B is adjusted in association with movement of the distal-end grip 26 of the medical treatment tool 2A. To be specific, the angle of the moving joint 25 of the medical treatment tool 2B is adjusted such that both the distal-end grips 26 (end effectors) are held in a parallel position relationship. Note here that both the distal-end grips 26 are not necessarily held in a parallel position relationship; they may be held in various angle configurations.

The controller 3 determines the control angle $\theta3$ of the slave medical treatment tool 2B (to be controlled) on the basis of sensor signals produced out of the first trocar 1A and the second trocar 1B and the control angle $\theta1$ of the master medical treatment tool 2A to control the driver 22b. Note here that the master tool may be changed by operation of the master/slave changeover input portion 213 over to the slave tool to be controlled, and vice versa. In that case, both must be medical treatment tools. The master/slave changeover input portion 213 may be provided on the grip members 27b of the medical treatment tools 2A and 2B or, alternatively, a footswitch or the like may separately be provided. There is a changeover between the master and the slave taking place for each operation of the master/slave changeover input portion 213. While FIG. 14 shows that the medical treatment tool 2A is used as the master and the tool 2B is used as the slave (to be controlled), it is to be noted that the master/slave changeover input portion 214 may be operated to change the medical treatment tool 2B over to the master and the medical treatment tool 2A over to the slave to be controlled: the moving joint of the medical treatment tool 2A may be controlled in association with the operation of the medical treatment tool 2B.

Figure 15:
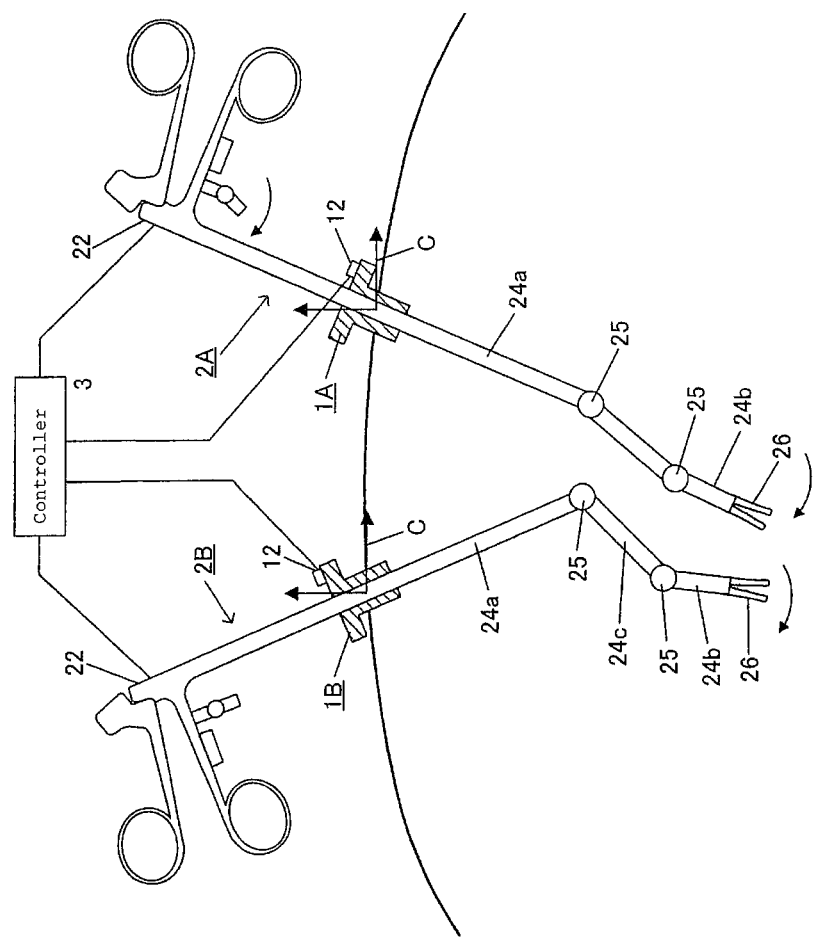
FIG. 15 is illustrative of the control mode (Example 6) of the medical treatment tool according to one embodiment of the invention.

FIG. 15 shows a control mode (Example 6) of controlling medical treatment tools according to a further embodiment of the invention. In Example 6, the medical treatment tool 2A (forceps) is used as the master, and the medical treatment tool 2B (forceps) is used as the slave to be controlled, too. The medical treatment tools 2A and 2B are each provided with a moving joint, and the direction input portion 211a of the master tool is operated to move the moving joint 25 of the master. As in FIG. 11, contact of the medical treatment tool 2A with the medical treatment tool 2B will be avoided, because each moving joint 25 of the slave medical treatment tool 2B is driven depending on the position of the moving joint 25 of the master medical treatment tool 2A. It is here to be noted that because the moving joint 25 is provided on the master side tool too, the controller 3 acquires a sensor signal from the first trocar 1A plus a state of the moving joint 25 on the master tool side. Then, the position of the medical treatment tool 2B inserted in place is determined on the sensor signal from the second trocar 1B to control each moving joint 25 of the medical treatment tool 2B such that both the tools 2A and 2B do not come into contact with each other.

Figure 16:
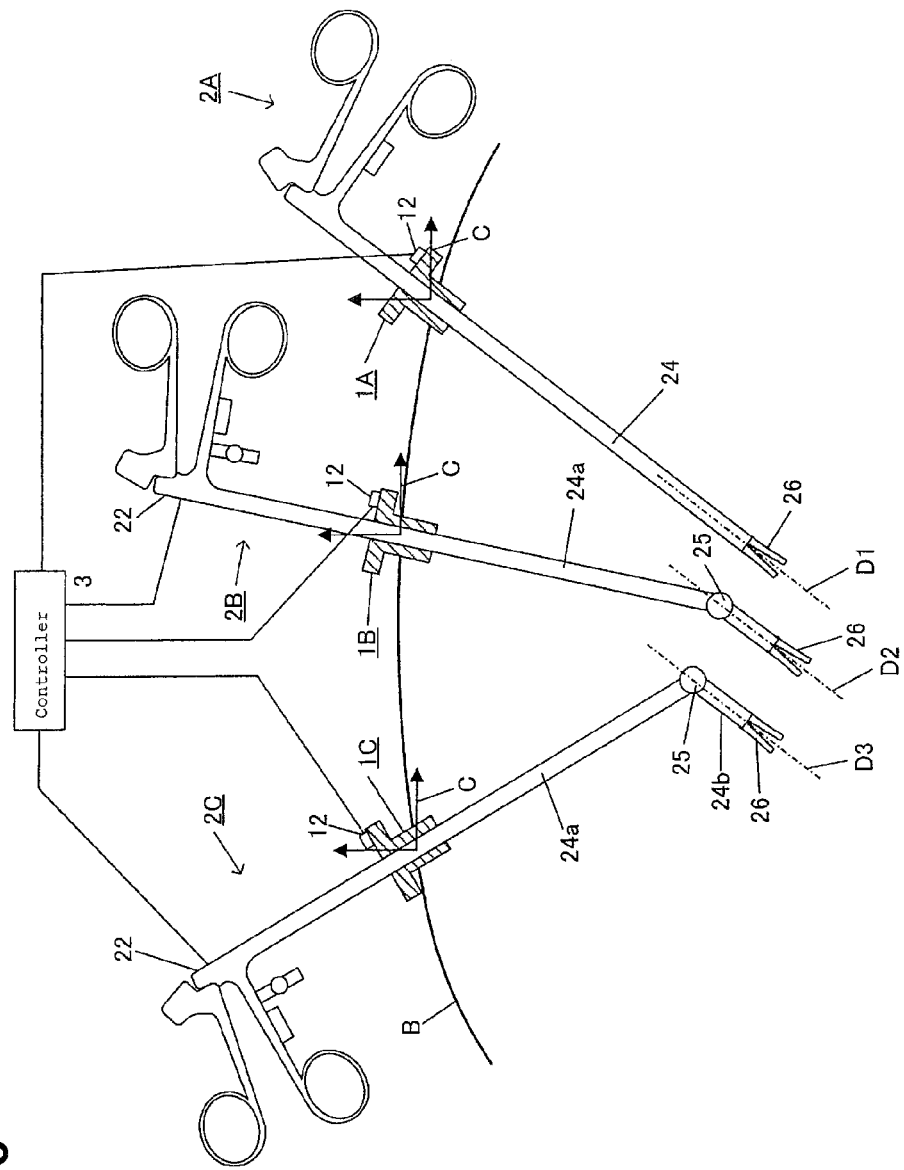
FIG. 16 is illustrative of the control mode (Example 7) of the medical treatment tool according to one embodiment of the invention.

While some mode embodiments concerning medical treatment tools have been described, it is to be noted that in the medical system of the invention, multiple medical treatment tools to be controlled may be provided. FIG. 16 shows a control mode (Example 7) of controlling medical treatment tools according to a further embodiment of the invention. In Example 7, the moving joints 25 of two medical treatment tools 2B and 2C (forceps here) to be controlled are driven in coordinated association with the movement of the master medical treatment tool 2A (forceps). In the follow-up processing according to the embodiment described here, the respective joints 25 are driven and controlled such that the directions D2 and D3 of the distal-end grip members 26 of the slave medical treatment tools 2B and 2C get parallel with the direction D1 of the distal-end grip member 26 of the master medical treatment tool 2A. While both the medical treatment tools 2B and 2C are shown in FIG. 16 to be controlled, it is to be appreciated that in the mode of controlling multiple medical treatment tools, one tool may be changed over to another based on the operation of the input unit. Such a mode contributes more to practitioner's operability because multiple medical treatment tools to be operated in coordinated association with one another may be actuated as a single unit. In the embodiment described here, too, the master/slave changeover input portion 213 may be operated or otherwise actuated for a changeover between the master tool and the slave tool.

While the present invention has been explained with reference to some embodiments according to certain aspects of the invention, it is to be appreciated that the invention is not limited to them; suitable combinations of the configurations of the respective embodiments are also included in the category of the invention.

EXPLANATION OF THE REFERENCE NUMERALS

1: Trocar
111: Upper housing
112: Lower housing
113: Tubular member
114: Cable
115: Insertion opening
116: Coupler
12: Trocar sensor assembly
121: Tilt angle detection sensor
122: Amount-of-movement detection sensor
122a: Amount-of-movement detection sensor
122b: Photosensor
123: Amount-of-rotation detection sensor
123a: Amount-of-rotation detection roller
123b: Photosensor
13: Communication unit
2: Medical instrument (or medical treatment tool)
21: Operation input unit
211: Direction input portion
212: Mode input portion
213: Master/slave changeover input portion
22: Driver
24a: First shaft
24b: Second shaft
25: Moving joint
26: Distal-end grip (end effector)
27,27a, 27b: Grip member
28: Imager
29: Water feed portion
3: Controller
31: Control unit
32: Memory

What is claimed is:

1. A medical system, comprising:
a slave medical treatment tool to be controlled, the slave medical treatment tool including a first shaft coupled to a first grip grasped by a user, a first end effector located at a distal end of the first shaft, a moving joint for adjusting an angle of the first end effector relative to the first shaft, and a driver for driving the moving joint;
a master medical instrument serving as a master control instrument, the master medical instrument including a second shaft coupled to a second grip grasped by the user and a second end effector located at a distal end of the second shaft;
a first trocar having an insertion opening through which the slave medical treatment tool is inserted;
a second trocar having an insertion opening through which the master medical instrument is inserted;
a sensor for producing out a sensor signal including at least an angle of the second effector; and
a controller that sets a follow-up criterion based on the sensor signal produced out of the sensor and enables follow-up processing for driving the driver such that the angle of the first end effector follows the follow-up criterion.

2. A medical system as recited in claim 1, wherein the sensor comprises a tilt angle detection sensor located at the second trocar or the master medical instrument.

3. A medical system as recited in claim 1, wherein the sensor comprises an amount-of-movement detection sensor for detecting an amount of rectilinear movement of the master medical instrument relative to the second trocar.

4. A medical system as recited in claim 1, wherein the sensor comprises an amount-of-rotation detection sensor for detecting an amount of rotation of the master medical instrument relative to the second trocar.

5. A medical system as recited in claim 1, further comprising a direction input portion of producing an operational signal based on operation, wherein the controller enables operation processing that drives the driver based on an operational signal from the direction input portion to adjust an angle of the first end effector.

6. A medical system as recited in claim 5, further comprising a mode input portion of producing a changeover signal based on operation, wherein the controller enables changeover processing that implements a changeover between the follow-up processing and the operation processing based on a mode signal from the mode input portion.

7. A medical system as recited in claim 1, wherein the master medical instrument includes a moving joint for adjusting an angle of the first end effector relative the first shaft.

8. A medical system as recited in claim 7, wherein the follow-up processing sets a follow-up criterion based on a sensor signal produced out of the sensor and a state of the moving joint of the master medical instrument.

9. A medical system as recited in claim 7, further comprising a master/slave changeover input portion that produces a changeover signal based on operation, wherein the controller enables changeover processing between the master medical instrument and the slave medical treatment tool based on a changeover signal from the master/slave changeover input portion.

10. A method of controlling a medical system, the medical system comprising:
a slave medical instrument configured to be inserted through a hole of a first trocar,
a master medical instrument configured to be inserted through a hole of a second trocar,
a second end effector located at a distal end of the slave medical instrument,
a sensor for producing out a sensor signal including at least an angle of the first end effector,
and
a driver for adjusting an angle of the second end effector, the method comprising:
detecting the sensor signal;
setting a follow-up criterion on the basis of the sensor signal; and
driving the driver on the basis of the follow-up criterion.

* * * * *